United States Patent
Dunagan et al.

(10) Patent No.: US 8,548,558 B2
(45) Date of Patent: Oct. 1, 2013

(54) ELECTRODE CAPABLE OF ATTACHMENT TO A GARMENT, SYSTEM, AND METHODS OF MANUFACTURING

(75) Inventors: Boyd Dunagan, Wabasha, MN (US);
Jay M. Dunagan, Wabasha, MN (US);
Erick Garstka, Westfield, MA (US);
Keith J. Geolat, Lake City, MN (US);
Charles A. Rowe, Winona, MN (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/005,636

(22) Filed: Jan. 13, 2011

(65) Prior Publication Data
US 2011/0130640 A1    Jun. 2, 2011

Related U.S. Application Data

(63) Continuation-in-part of application No. 12/043,266, filed on Mar. 6, 2008.

(51) Int. Cl.
*A61B 5/04* (2006.01)
*A61N 1/00* (2006.01)

(52) U.S. Cl.
USPC ............ 600/391; 600/382; 600/394; 607/152

(58) Field of Classification Search
USPC ................. 600/386, 388–392; 607/149, 152, 607/153
See application file for complete search history.

(56) References Cited

U.S. PATENT DOCUMENTS

| | | | |
|---|---|---|---|
| 3,998,215 A * | 12/1976 | Anderson et al. | ............ 600/397 |
| 4,391,279 A | 7/1983 | Stein | |
| 4,537,198 A | 8/1985 | Corbett | |
| 4,580,572 A | 4/1986 | Granek et al. | |
| 4,583,547 A | 4/1986 | Granek et al. | |
| 4,583,549 A | 4/1986 | Manoli | |
| 4,608,987 A | 9/1986 | Mills | |
| 4,685,467 A | 8/1987 | Cartmell et al. | |
| 4,694,835 A | 9/1987 | Strand | |
| 4,698,848 A | 10/1987 | Buckley | |

(Continued)

FOREIGN PATENT DOCUMENTS

| | | |
|---|---|---|
| GB | 2 457 025 A | 8/2009 |
| WO | WO 99/39635 A1 | 8/1999 |
| WO | WO 2009/041496 A1 | 4/2009 |

OTHER PUBLICATIONS

European Search Report corresponding to European Application No. EP 09 25 0570; completed Nov. 11, 2009; 6 pages.

*Primary Examiner* — Linda Dvorak
*Assistant Examiner* — Brian M Antiskay
(74) *Attorney, Agent, or Firm* — Lisa E. Wisnor, Esq.

(57) ABSTRACT

An electrode for selective attachment to at least one of a garment and a subject, is provided and includes a conductive member defining a first side and a second side; a conductive composition disposed on the first side of the conductive member, wherein the conductive composition has a first adhesive strength; a contact layer disposed on the second side of the conductive member, wherein the contact layer includes a pressure sensitive adhesive portion and a conductive hydrogel portion, wherein the pressure sensitive adhesive portion has a second adhesive strength that is greater than the adhesive strength of the conductive composition; whereby the electrode is adherable to the garment and to the subject such that the conductive composition is adhered to the subject and the pressure sensitive adhesive portion is adhered to the garment, wherein removal of the garment from the subject results in removal of the electrode from the subject.

26 Claims, 6 Drawing Sheets

(56) References Cited

U.S. PATENT DOCUMENTS

| | | | |
|---|---|---|---|
| 4,700,710 | A | 10/1987 | Hoffman |
| 4,709,702 | A | 12/1987 | Sherwin |
| 4,729,377 | A | 3/1988 | Granek et al. |
| 4,763,660 | A | 8/1988 | Kroll et al. |
| 4,809,700 | A | 3/1989 | Castelli |
| 4,832,608 | A | 5/1989 | Kroll |
| 4,838,273 | A | 6/1989 | Cartmell |
| 4,852,572 | A | 8/1989 | Nakahashi et al. |
| 4,867,166 | A | 9/1989 | Axelgaard et al. |
| 4,889,131 | A | 12/1989 | Salem et al. |
| 4,911,169 | A | 3/1990 | Ferrari |
| 4,928,696 | A | 5/1990 | Henderson et al. |
| 4,967,038 | A | 10/1990 | Gevins et al. |
| 4,996,989 | A | 3/1991 | Stundel et al. |
| 5,016,636 | A | 5/1991 | Kulskowski |
| 5,022,412 | A | 6/1991 | Gracovetsky et al. |
| 5,038,796 | A | 8/1991 | Axelgaard et al. |
| 5,042,481 | A | 8/1991 | Suzuki et al. |
| 5,078,138 | A | 1/1992 | Strand et al. |
| 5,119,816 | A | 6/1992 | Gevins |
| 5,121,747 | A | 6/1992 | Andrews |
| 5,169,380 | A | 12/1992 | Brennan |
| 5,184,620 | A | 2/1993 | Cudahy et al. |
| 5,224,479 | A | 7/1993 | Sekine |
| 5,313,942 | A | 5/1994 | Platzker |
| 5,313,952 | A | 5/1994 | Hoch |
| 5,341,806 | A | 8/1994 | Gadsby et al. |
| 5,353,793 | A | 10/1994 | Bornn |
| 5,356,428 | A | 10/1994 | Way |
| 5,370,116 | A | 12/1994 | Rollman et al. |
| 5,374,283 | A | 12/1994 | Flick |
| 5,443,494 | A | 8/1995 | Paolizzi et al. |
| 5,445,149 | A | 8/1995 | Rotolo et al. |
| 5,450,845 | A | 9/1995 | Axelgaard |
| 5,458,141 | A | 10/1995 | Nell |
| 5,462,157 | A | 10/1995 | Freeman et al. |
| 5,466,244 | A | 11/1995 | Morgan |
| 5,479,934 | A | 1/1996 | Imran |
| 5,487,759 | A | 1/1996 | Bastyr et al. |
| 5,511,548 | A | 4/1996 | Riazzi et al. |
| 5,518,007 | A | 5/1996 | Becker |
| 5,617,853 | A | 4/1997 | Morgan |
| 5,643,329 | A | 7/1997 | Solomonow et al. |
| 5,645,062 | A | 7/1997 | Anderson et al. |
| 5,645,063 | A | 7/1997 | Straka, Jr. |
| 5,782,238 | A | 7/1998 | Beitler |
| 5,785,040 | A | 7/1998 | Axelgaard |
| 5,800,351 | A | 9/1998 | Mann |
| 5,846,198 | A | 12/1998 | Killmann |
| 5,868,671 | A | 2/1999 | Mahoney |
| 5,871,534 | A | 2/1999 | Messick et al. |
| 5,938,597 | A | 8/1999 | Stratbucker |
| 6,032,060 | A | 2/2000 | Carim et al. |
| 6,032,064 | A | 2/2000 | Devlin et al. |
| 6,047,203 | A | 4/2000 | Sackner et al. |
| 6,064,901 | A | 5/2000 | Cartmell et al. |
| 6,065,154 | A | 5/2000 | Hulings et al. |
| 6,067,464 | A | 5/2000 | Musha |
| 6,134,480 | A | 10/2000 | Minogue |
| 6,151,528 | A | 11/2000 | Maida |
| 6,154,669 | A | 11/2000 | Hunter et al. |
| 6,161,030 | A | 12/2000 | Levendowski et al. |
| 6,178,357 | B1 | 1/2001 | Gliner et al. |
| 6,198,955 | B1 | 3/2001 | Axelgaard et al. |
| 6,219,568 | B1 | 4/2001 | Kelly et al. |
| 6,259,939 | B1 | 7/2001 | Rogel |
| 6,272,365 | B1 | 8/2001 | Ronkainen et al. |
| 6,327,487 | B1 | 12/2001 | Stratbucker |
| 6,341,229 | B1 | 1/2002 | Akiva |
| 6,341,237 | B1 | 1/2002 | Hurtado |
| 6,381,481 | B1 | 4/2002 | Levendowski et al. |
| 6,381,482 | B1 | 4/2002 | Jayaraman et al. |
| 6,393,317 | B1 | 5/2002 | Fukuda et al. |
| 6,408,200 | B1 | 6/2002 | Takashina |
| 6,418,333 | B1 | 7/2002 | Axelgaard |
| 6,438,428 | B1 | 8/2002 | Axelgaard et al. |
| 6,441,747 | B1* | 8/2002 | Khair et al. ............... 340/870.16 |
| 6,450,942 | B1 | 9/2002 | Lapanashvili et al. |
| 6,453,203 | B1 | 9/2002 | Yamazaki et al. |
| 6,456,872 | B1 | 9/2002 | Falsandler |
| 6,477,397 | B1 | 11/2002 | Ronkainen et al. |
| 6,480,731 | B1 | 11/2002 | DeLuca et al. |
| 6,510,340 | B1 | 1/2003 | Jordan |
| 6,532,379 | B2 | 3/2003 | Stratbucker |
| 6,546,291 | B2 | 4/2003 | Merfeld et al. |
| 6,551,252 | B2 | 4/2003 | Sackner et al. |
| 6,553,247 | B1 | 4/2003 | Rytky |
| 6,560,473 | B2 | 5/2003 | Dominguez |
| 6,567,706 | B2 | 5/2003 | Bar-Or et al. |
| 6,571,115 | B2 | 5/2003 | Axelgaard et al. |
| 6,574,513 | B1 | 6/2003 | Collura et al. |
| 6,600,942 | B2 | 7/2003 | Nissila et al. |
| 6,640,122 | B2 | 10/2003 | Manoli et al. |
| 6,654,626 | B2 | 11/2003 | Devlin et al. |
| 6,687,523 | B1 | 2/2004 | Jayaramen et al. |
| 6,711,427 | B1 | 3/2004 | Ketelhohn |
| 6,735,481 | B1 | 5/2004 | Bingham et al. |
| 6,745,062 | B1 | 6/2004 | Finneran et al. |
| 6,745,082 | B2 | 6/2004 | Axelgaard |
| 6,755,795 | B2 | 6/2004 | Marmaropoulos |
| 6,757,916 | B2 | 7/2004 | Mah et al. |
| 6,775,566 | B2 | 8/2004 | Nissila |
| 6,778,862 | B2 | 8/2004 | Axelgaard et al. |
| 6,788,979 | B1 | 9/2004 | Axelgaard et al. |
| 6,832,982 | B1 | 12/2004 | Lapanashvili et al. |
| 6,840,955 | B2 | 1/2005 | Ein |
| 6,847,836 | B1 | 1/2005 | Sujdak |
| 6,850,791 | B1 | 2/2005 | Axelgaard et al. |
| 6,915,148 | B2 | 7/2005 | Finneran et al. |
| 6,917,825 | B2 | 7/2005 | Finneran et al. |
| 6,952,605 | B1 | 10/2005 | Scarberry |
| 6,973,344 | B2 | 12/2005 | Finneran et al. |
| 7,027,877 | B2 | 4/2006 | Dupelle et al. |
| 7,039,468 | B2 | 5/2006 | Freed et al. |
| 7,062,309 | B2 | 6/2006 | Ryu et al. |
| 7,069,089 | B2 | 6/2006 | Minogue et al. |
| 7,072,721 | B1 | 7/2006 | Trent |
| RE39,250 | E | 8/2006 | Freeman et al. |
| 7,127,279 | B2 | 10/2006 | Finneran et al. |
| 7,130,692 | B2 | 10/2006 | Brighton et al. |
| 7,158,822 | B2 | 1/2007 | Payne, Jr. |
| 7,177,705 | B2 | 2/2007 | Cohen |
| 7,187,985 | B2* | 3/2007 | Carim ............................ 607/152 |
| 7,233,828 | B2 | 6/2007 | Vlad |
| 7,254,447 | B2 | 8/2007 | Campos et al. |
| 7,299,084 | B1 | 11/2007 | Price |
| 7,315,754 | B2 | 1/2008 | Leonhardt et al. |
| 2001/0044573 | A1 | 11/2001 | Manoli et al. |
| 2002/0029005 | A1 | 3/2002 | Levendowski et al. |
| 2002/0032475 | A1 | 3/2002 | Arbel |
| 2002/0058982 | A1 | 5/2002 | Axelgaard et al. |
| 2002/0068861 | A1 | 6/2002 | Yang |
| 2002/0077688 | A1 | 6/2002 | Kirkland |
| 2002/0077689 | A1 | 6/2002 | Kirkland |
| 2002/0082491 | A1 | 6/2002 | Nissila |
| 2002/0091313 | A1 | 7/2002 | Feucht et al. |
| 2002/0123679 | A1 | 9/2002 | Dominguez |
| 2002/0133069 | A1 | 9/2002 | Roberts |
| 2002/0138125 | A1 | 9/2002 | Axelgaard et al. |
| 2002/0143373 | A1 | 10/2002 | Courtnage et al. |
| 2002/0151951 | A1 | 10/2002 | Axelgaard et al. |
| 2002/0183605 | A1 | 12/2002 | Devlin et al. |
| 2003/0045922 | A1 | 3/2003 | Northrop |
| 2003/0083559 | A1* | 5/2003 | Thompson .................... 600/372 |
| 2003/0120183 | A1 | 6/2003 | Simmons |
| 2003/0187341 | A1 | 10/2003 | Sackner et al. |
| 2003/0212319 | A1 | 11/2003 | Magill |
| 2004/0030270 | A1 | 2/2004 | Johnson |
| 2004/0054273 | A1 | 3/2004 | Finneran et al. |
| 2004/0054274 | A1 | 3/2004 | Finneran et al. |
| 2004/0054275 | A1 | 3/2004 | Finneran et al. |
| 2004/0054276 | A1 | 3/2004 | Finneran et al. |
| 2004/0073271 | A1 | 4/2004 | Harry et al. |
| 2004/0138546 | A1 | 7/2004 | Reho et al. |

| | | | | | | |
|---|---|---|---|---|---|---|
| 2004/0143313 A1 | 7/2004 | Chang et al. | 2006/0135863 A1* | 6/2006 | Birnbaum et al. | 600/388 |
| 2004/0172115 A1 | 9/2004 | Miazga et al. | 2006/0135884 A1 | 6/2006 | Hack et al. | |
| 2004/0210165 A1 | 10/2004 | Marmaropoulos et al. | 2006/0142654 A1 | 6/2006 | Rytky | |
| 2004/0230226 A1 | 11/2004 | Bingham et al. | 2006/0167353 A1 | 7/2006 | Nazeri | |
| 2004/0236202 A1 | 11/2004 | Burton | 2006/0190057 A1 | 8/2006 | Reese | |
| 2004/0254624 A1 | 12/2004 | Johnson | 2006/0211934 A1 | 9/2006 | Hassonjee et al. | |
| 2004/0260166 A1 | 12/2004 | Merilainen | 2006/0247733 A1 | 11/2006 | Amer | |
| 2004/0260167 A1 | 12/2004 | Leonhardt et al. | 2006/0258914 A1 | 11/2006 | Derchak et al. | |
| 2004/0260376 A1 | 12/2004 | Craige, III et al. | 2007/0010750 A1 | 1/2007 | Ueno et al. | |
| 2004/0267231 A1* | 12/2004 | Sun et al. ............ 604/500 | 2007/0027387 A1 | 2/2007 | Fendrock | |
| 2005/0004489 A1 | 1/2005 | Sarkela et al. | 2007/0038057 A1 | 2/2007 | Narn et al. | |
| 2005/0010096 A1 | 1/2005 | Blackadar | 2007/0038252 A1 | 2/2007 | Carroll | |
| 2005/0010264 A1 | 1/2005 | Brighton et al. | 2007/0049814 A1 | 3/2007 | Muccio | |
| 2005/0020935 A1 | 1/2005 | Helzel et al. | 2007/0078324 A1* | 4/2007 | Wijisiriwardana | 600/386 |
| 2005/0054941 A1 | 3/2005 | Ting et al. | 2007/0083096 A1 | 4/2007 | Paradiso | |
| 2005/0090867 A1 | 4/2005 | Lapanashvili et al. | 2007/0093706 A1 | 4/2007 | Gevins et al. | |
| 2005/0113661 A1 | 5/2005 | Nazeri et al. | 2007/0106343 A1 | 5/2007 | Monogue et al. | |
| 2005/0124901 A1 | 6/2005 | Misczynski et al. | 2007/0112262 A1 | 5/2007 | Payne, Jr. | |
| 2005/0137472 A1 | 6/2005 | Ryu et al. | 2007/0118032 A1 | 5/2007 | Finneran et al. | |
| 2005/0197556 A1 | 9/2005 | Stoler | 2007/0225585 A1 | 9/2007 | Washbon et al. | |
| 2005/0203591 A1 | 9/2005 | Brighton | 2007/0238945 A1 | 10/2007 | Delic et al. | |
| 2005/0245834 A1* | 11/2005 | Baumer et al. ............ 600/528 | 2007/0239212 A1 | 10/2007 | Schneider et al. | |
| 2005/0251003 A1 | 11/2005 | Istvan et al. | 2007/0293911 A1 | 12/2007 | Crowe et al. | |
| 2005/0277821 A1 | 12/2005 | Payne, Jr. | 2008/0143080 A1 | 6/2008 | Burr | |
| 2006/0084855 A1 | 4/2006 | Teschner et al. | | | | |
| 2006/0117805 A1 | 6/2006 | Valentine et al. | * cited by examiner | | | |

ELECTRODE CAPABLE OF ATTACHMENT TO A GARMENT, SYSTEM, AND METHODS OF MANUFACTURING

CROSS REFERENCE TO RELATED APPLICATIONS

This application claims priority under 35 U.S.C 120 as a continuation-in-part to co-pending U.S. patent application Ser. No. 12/043,266, filed Mar. 6, 2008, entitled BIOMEDICAL ELECTRODE, which is incorporated herein by reference in its entirety for all purposes.

BACKGROUND

1. Technical Field

The present disclosure generally relates to electrodes and, more particularly, to wire-free and stud-free electrode assemblies capable of use in connection with a garment.

2. Discussion of Related Art

Skin-applied electrode assemblies are well known for use in medical applications such as cardiac pacing, electrocardiograph (ECG) monitoring, and defibrillation. Typically, these electrode assemblies are attached to a wire lead or cable that is attached at its opposite end to a connector of a medical device or medical device instrumentation. Electrode assemblies generally include an electrode, e.g., a conductor such as a thin layer of metal, resting on a foam backing. The electrode is typically covered with a conductive gel that contacts a patient's skin. In addition, for one or more reasons, e.g., to prevent the adhesive gel from drying out, to maintain the electrodes in a sanitary condition, and to cover the adhesive until a caregiver is ready to adhere the electrode to the patient, a release sheet, e.g., a plastic cover, is positioned over the adhesive and/or conductive gel of each electrode.

Concerning the operation and functionality of electrodes, electrodes are used to transmit electrical signals between the body of patient and external medical equipment, such as a monitoring, diagnostic, or stimulating device. It has been known that electrical signals, which are obtained via electrodes applied to the body, can be evaluated in connection with various diagnostic procedures. The application of electrodes on the body surface should provide reliability and stability of position. Thus, large contact areas are used for obtaining signals in a reliable manner in order to ensure acceptable electric contact between the electrode and the skin of a patient. Two basic principles have become widespread for attaching electrodes to the skin of a patient. Electrodes are either attached to the body surface as individually adhering electrodes or the electrodes are attached to a carrier means, which ensures the reliable seating of the electrodes in one or more desired positions.

Concerning the different types of electrodes, conventional electrodes may include passive electrodes and active electrodes. Passive electrodes include a metal disc with a connecting wire to electronic circuitry. This simplicity makes this type of electrode low cost. However, these electrodes are prone to noise and can require numerous noise canceling techniques to achieve satisfactory performance. One noise canceling technique, to minimize impedance at the skin-electrode interface and to minimize interference, involves conditioning the skin where the electrode is to be applied. On the other hand, active electrodes may include resistive and capacitive active electrodes. Resistive active electrodes use a direct current path between the subject's skin and the input of an operational amplifier to acquire a signal. Capacitive active electrodes do not make electrical contact with the subject's skin, but have a capacitive link between subject's skin and the electrode.

Biomedical electrodes, as described in the present disclosure, are resistive active electrodes. Biomedical electrodes are commonly used in therapeutic and diagnostic medical applications including, e.g., a variety of signal based rehabilitative procedures, ECG or transcutaneous electrical nerve stimulation (TENS) procedures, maternal and/or fetal monitoring. Conventional biomedical electrodes are secured to the skin of a patient via a hydrogel and/or pressure sensitive adhesive. Hydrogels used in the construction of biomedical electrodes constitute a broad class of materials which swell extensively in water but are not completely water soluble. Such hydrogels are used in a variety of biomedical applications and may be applied in bulk forms which vary from clear to opaque and from a relatively stiff to a relatively soft consistency. Sometimes the bulk forms are reinforced by woven fabrics to increase the composite strength. Hydrogels have also been used as coatings for various biomedical applications.

In addition to using hydrogels for providing a secure connection between the electrode and the skin of a patient, an electrical cable or lead wire or metal stud is used to place the electrode in communication with an external electrical source. Various mechanisms for connecting a male/female terminal of the electrode to the complementary male/female terminal of the lead wire typically include "snap on" connectors, "pinch clip" arrangements, "twist on" couplings or magnetic couplings.

However, the arranging of a lead wire or metal stud on an electrode patch not only will increase the thickness of the resulting electrode patch, but also it will cause discomfort to any person attached thereby. Accordingly, a need exists for an electrode in which the lead wire or metal stud is removed. Additionally, a need exists for a wire-free and stud-free electrode capable of being attached to a garment, such electrode including a first side supporting a hydrogel having a first adhesive quality or property for selective or removable fixation to the skin of a patient, and second side supporting at least a pressure sensitive adhesive (PSA) having a second adhesive quality or property for selective or removable fixation to the garment.

SUMMARY

The present disclosure relates to wire-free and/or stud-free electrode assemblies capable of use in connection with a garment.

According to an aspect of the present disclosure, an electrode for selective attachment to at least one of a garment and a subject, is provided. The electrode includes a conductive member defining a first side and a second side; a conductive composition disposed on the first side of the conductive member, wherein the conductive composition has a first adhesive strength; and a contact layer disposed on the second side of the conductive member, wherein the contact layer includes a pressure sensitive adhesive portion and a conductive hydrogel portion, wherein the pressure sensitive adhesive portion has a second adhesive strength that is greater than the adhesive strength of the conductive composition. The electrode is adherable to the garment and to the subject such that the conductive composition is adhered to the subject and the pressure sensitive adhesive portion is adhered to the garment, wherein removal of the garment from the subject results in removal of the electrode from the subject.

The conductive composition may be a hydrogel. The hydrogel portion of the contact layer may have an adhesive strength that is less than the second adhesive strength of the pressure sensitive adhesive. The hydrogel portion of the contact layer may extend at least partially across a length of the electrode. The hydrogel portion of the contact layer may extend completely across the length of the electrode, and wherein a pressure sensitive adhesive portion may be provided on opposed sides of the hydrogel portion. The pressure sensitive adhesive portion of the contact layer may completely surround the hydrogel portion.

The electrode may further include a layer of a silver composition interposed between the conductive member and the conductive composition. The layer of silver composition may be a layer of Silver/Silver-Chloride (Ag/AgCl). The layer of Silver/Silver-Chloride (Ag/AgCl) may be in the form of a coating of Silver/Silver-Chloride (Ag/AgCl) ink that is deposited or flooded on an underlying layer.

According to another aspect of the present disclosure, an electrode is provided and includes a first layer adapted for selective disposition on a garment; a second layer adapted for selective disposition on a subject; and a third layer adapted for disposition and electrical communication between the first layer and the second layer. At least one portion of the first layer includes a hydrogel and at least one portion of the first layer includes a pressure sensitive adhesive.

According to a further aspect of the present disclosure, an electrode system for selective use with a subject is provided and include a garment having a first side and a second side; and at least one electrode for selective attachment to the first side of the garment and for selective attachment to the subject. The electrode includes a first layer adapted for selective engagement on the garment; a second layer adapted for selective engagement on the subject; and a third layer interposed between the first layer and the second layer, the third layer providing for electrical communication between the first layer and the second layer. At least one portion of the first layer includes a hydrogel and at least one portion of the first layer includes a pressure sensitive adhesive.

According to still another aspect of the present disclosure, a method of manufacturing an electrode is provided. The method includes the steps of providing an electrically conductive layer having a first side and a second side; depositing a first layer on the first side of the electrically conductive layer; and depositing a second layer on the second side of the electrically conductive layer. The first layer is adapted for selective disposition on a garment, the second layer is adapted for selective disposition on a subject, and the electrically conductive layer provides for electrical communication between the first layer and the second layer. At least one portion of the first layer includes a conductive hydrogel and at least one portion of the first layer includes a pressure sensitive adhesive.

The at least one portion of the hydrogel may have a first adhesive strength, and wherein the at least one portion of the pressure sensitive adhesive may have a second adhesive strength. The second adhesive strength may be greater than the first adhesive strength.

The electrode may further include a release liner selectively and removably adhered to at least one of a surface of the first layer and a surface of the second layer.

The pressure sensitive adhesive of the first layer may be a double-coated non-conductive film. The hydrogel of the first layer may be a conductive hydrogel. The second layer may be a conductive hydrogel layer. The conductive hydrogel of the second layer may be similar to the hydrogel of the first layer.

The third layer may be a carbon vinyl conductive layer.

The hydrogel of the first layer may be of a circular shape centrally disposed on the electrode such that the pressure sensitive adhesive at least partially surrounds the hydrogel. The hydrogel of the first layer may define a strip extending across the electrode to divide the electrode into three sections such that the hydrogel separates the pressure sensitive adhesive.

The electrode is a wire-less electrode.

According to yet another aspect of the present disclosure, a method of manufacturing an electrode system for selective use with a subject is provided. The method includes the steps of providing a garment having a first side and a second side; providing at least one electrode for selective attachment to the first side of the garment and for selective attachment to the subject; providing an electrically conductive layer having a first side and a second side; depositing a first layer on the first side of the electrically conductive layer; and depositing a second layer on the second side of the electrically conductive layer. The first layer is adapted for selective disposition on a garment, the second layer is adapted for selective disposition on a subject, and the electrically conductive layer provides for electrical communication between the first layer and the second layer; and wherein at least one portion of the first layer includes a conductive hydrogel and at least one portion of the first layer includes a pressure sensitive adhesive.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

The exemplary embodiments of the electrodes as a component of a reusable multi-electrode garment system disclosed herein are discussed in terms of use in performing a surgical therapeutic or diagnostic procedure in delivering or collecting electrical signals relative to a subject. Such procedures are inclusive of, but, not limited to, a variety of signal based rehabilitative procedures, muscle stimulation, electrocardiograph procedures, maternal and/or fetal monitoring.

In the discussion that follows, the term "subject" refers to a human patient or other animal. The term "clinician" refers to a doctor, nurse or other care provider and may include support personnel.

Figure 1A:
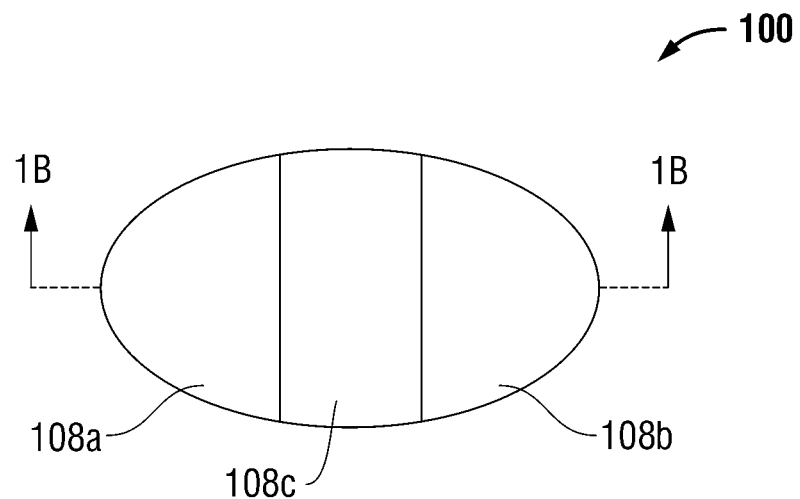
FIG. 1A is a top view of an electrode having a hydrogel portion that separates a pressure sensitive adhesive, in accordance with the present disclosure.
Figure 1B:
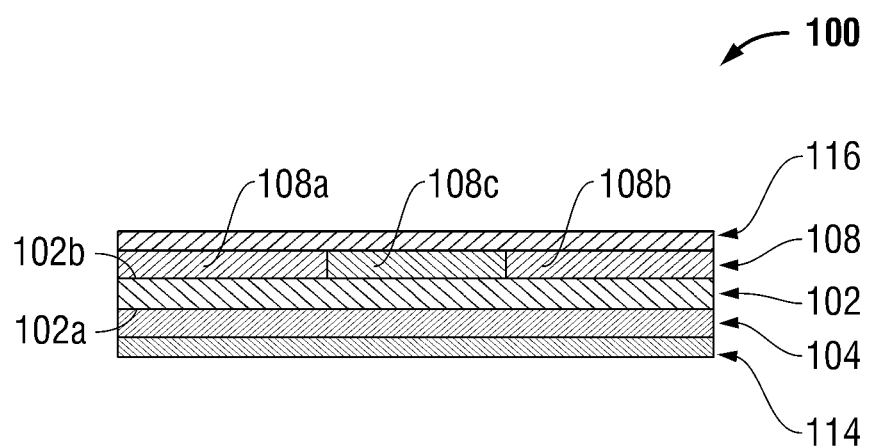
FIG. 1B is a cross-sectional view of the electrode of FIG. 1A, in accordance with the present disclosure.
Figure 1C:
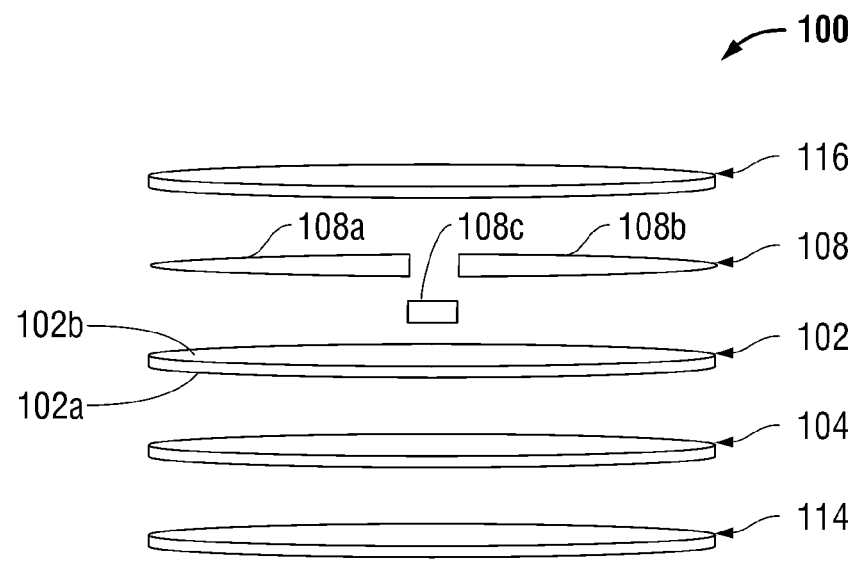
FIG. 1C is an exploded cross-section side view of the electrode of FIG. 1B, in accordance with the present disclosure.
Figure 1D:
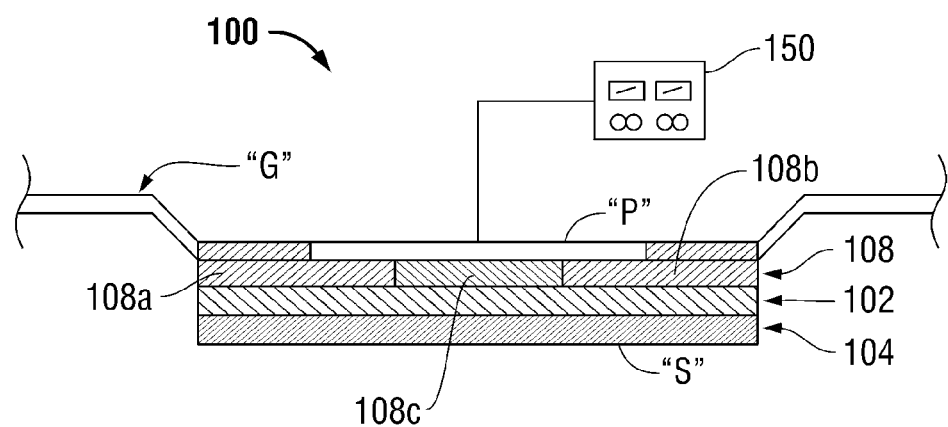
FIG. 1D is a cross-sectional view of the electrode in FIG. 1B without liners, connected to a treatment device and affixed to a garment and a subject.

Electrode 100 is configured for selective attachment or affixation to a garment "G" and for selective attachment or affixation to a subject "S", e.g., to the skin of the subject "S" (see FIG. 1D). Electrode 100 includes a first layer or conductive member 102 defining a first or skin side 102a relative to the subject "S" and a second or garment side 102b, opposite first side 102a. Conductive member 102 may be made from a conductive carbon, aluminum, tin, copper, silver or any other suitable material. As a further alternative, conductive member 102 may comprise a conductive plastic material or conductive carbon vinyl. Conductive member 102 may include a coating of a silver composition (not shown) on either or both the skin and garment sides 102a and 102b thereof, respectively.

Electrode 100 further includes a second layer or conductive composition 104 disposed adjacent skin side 102a of the conductive member 102 for application/adhesion to or contact with the skin of subject "S." Conductive composition 104 may be made from, for example, but not limited to, Promeon RG-63B hydrogel (TycoHealthcare Group LP d/b/a Covidien). In some embodiments, conductive composition 104 may incorporate a woven and/or nonwoven cloth or gauze material (e.g., scrim) embedded therewithin or supporting the structure of the hydrogel. The conductive composition 104 may be any different commercially available conductive hydrogel.

In certain embodiments it may be desirable to provide a layer of adhesive (not shown) interposed between conductive member 102 and conductive composition 104.

A first or skin side release liner 114 is releasably secured to conductive composition 104. Release liner 114 can be made from a film or paper substrate having a release coating on one or both sides, such as, for example silicone. Release liner 114 protects and/or preserves conductive composition 104 (e.g., the hydrogel) and is removed prior to application on the skin of the subject 10. Release liner 114 may be applied to conductive composition 104 after use of electrode 100 to preserve the conductive composition 104 for subsequent use.

In an embodiment, electrode 100 further includes a third or contact layer 108 disposed adjacent garment side 102b of conductive member 102. In certain embodiments, contact layer 108 may overlie a layer of a silver composition, e.g., Silver/Silver-Chloride.

Contact layer 108 includes a first pressure sensitive adhesive (PSA) portion 108a, a second pressure sensitive adhesive (PSA) portion 108b, and a hydrogel portion 108c disposed between first and second pressure sensitive adhesive portions 108a, 108b, and extending at least partially across, and preferably entirely across, electrode 100. In one embodiment, hydrogel portion 108c extends entirely across electrode 100.

In particular, hydrogel portion 108c defines a strip extending across electrode 100 to contact layer 108 into three sections, such that hydrogel portion 108c separates the pressure sensitive adhesive into first pressure sensitive adhesive portion 108a and second pressure sensitive adhesive portion 108b.

Hydrogel portion 108c of contact layer 108 defines a conductive portion whereas pressure sensitive adhesive portions 108a, 108b define non-conductive portions (double-coated films). Hydrogel portion 108c of contact layer 108 may be made from, for example, but not limited to, Promeon RG-63B hydrogel (available from Tyco Health Care Group d/b/a Covidien).

First pressure sensitive adhesive portion 108a and second pressure sensitive adhesive portion 108b are configured, adapted, dimensioned, and/or selected to enable selective attachment of electrode 100 to a garment (not shown). Pressure sensitive adhesive portions 108a, 108b may be hot melt, acrylic, and/or rubber based adhesives. In one embodiment, pressure sensitive adhesive portions 108a, 108b are made substantially from non-conductive acrylic adhesives. As shown in FIG. 1D, first pressure sensitive adhesive portion 108a and second pressure sensitive pressure adhesive portion 108b may abut hydrogel portion 108c. Alternatively, one or both of first pressure sensitive adhesive portion 108a and second pressure sensitive adhesive portion 108b may overlap on the garment side one or more edges of hydrogel portion 108c.

Hydrogel portion 108c has a first adhesive strength and each of pressure sensitive adhesive portions 108a, 108b have a second adhesive strength greater than the first adhesive strength of hydrogel portion 108c (i.e., more aggressive). In other words, pressure sensitive adhesive portions 108a, 108b are more conducive to establishing a more secure attachment of electrode 100 to a garment than hydrogel portion 108c. Thus, the adhesive characteristics or properties of pressure sensitive adhesive portions 108a, 108b relative to a garment "G" are greater than the adhesive characteristics or properties of hydrogel portion 108c relative to the garment "G." As such, in one embodiment in which the first pressure sensitive adhesive portion 108a and the second pressure sensitive adhesive portion 108b overlaps a portion of the perimeter of hydrogel portion 108c, both first and second pressure sensitive adhesive portions 108a and 108b may provide additional adhesive support so that the hydrogel portion may remain with the electrode during application and removal to the garment. The pressure sensitive adhesive portion overlap is advantages in that it allows repeated application and removal to the garment which may be desired prior and subsequent to washing the garment. The pressure sensitive adhesive portion overlap may also enable the user to reposition an electrode previously applied to the garment.

A second release liner 116 is positioned to cover contact layer 108. First and second release liners 114 and 116 may each be made from poly-coated paper having a thickness of about 0.127 millimeters (mm) (about 0.005 inches or 5 mils).

As so configured, an electrical path is created from hydrogel portion 108c of contact layer 108, through conductive member 102, and to conductive composition 104, and vice-versa. As such, no lead wires or electrical snaps are provided for establishing electrical connection of conductive member 102 and/or conductive composition 104 with a therapeutic treatment or diagnostic treatment device.

It is contemplated that, additional conductive members may be positioned between conductive member 102 and contact layer 108, or between conductive member 102 and conductive composition 104 in a variety of different configurations. Such additional conductive members may be made from a conductive carbon, aluminum, tin, copper, silver or any other suitable material. As a further alternative, the additional conductive members may comprise a conductive plastic material. The additional conductive members may further include a coating of a silver composition on either or both the skin and garment sides thereof, respectively.

Referring again to FIG. 1A to FIG. 1D, in one method of application and use of electrode 100, first release liner 116, overlying contact layer 108, that is to be adjacent to the garment "G," is removed from contact layer 108 and electrode 100 is applied or adhered to garment "G" at a predefined location (e.g., at a location on garment "G" having a conductive pad "P," grid or the like). Such predefined location will correspond to a selected area of the body of the subject "S," wearing garment "G," to be treated or monitored, or a designated area on garment "G" having a conductive pad "P," grid, or the like, capable of electrical communication with electrode 100. Electrode 100 is applied or adhered to garment "G" such that hydrogel portion 108c of contact layer 108 is in electrical contact with conductive pad "P" of garment "G."

A number of electrodes according to the present disclosure, may be mounted to garment "G" at various preselected locations (as described below with reference to FIG. 3). Following fixation of electrode 100 to garment "G", second release liner 114 is removed from conductive composition 104 that is to contact the skin of the subject "S." Thereafter, garment "G" is applied to the subject "S" with electrodes 100 being positioned at the desired body locations. Pressure may be applied to the external surface of garment "G" adjacent electrode 100 to secure conductive composition 104 to the skin of the subject "S."

A therapeutic or diagnostic treatment may then be performed on the subject "S" through the at least one electrode 100. In particular, as seen in FIG. 1D, each conductive pad "P" is connected to a therapeutic treatment or diagnostic treatment device 150 and therapeutic/diagnostic signals are communicated between the treatment device 150 and the subject "S," via an electrical path created from the subject "S," to conductive composition 104, to conductive member 102, to hydrogel portion 108c, to conductive pad "P," and to the treatment device 150.

Upon completion of the procedure, garment "G" is removed from the subject "S." During removal of garment "G," due to the more aggressive nature of the pressure sensitive adhesive portions 108a, 108b as compared to that of conductive composition 104, the at least one electrode 100 remains adhered to garment "G" and is pulled away from the skin of the subject "S" as garment "G" is removed. Electrodes 100 may then be removed from garment "G."

More particularly, since the bond between pressure sensitive adhesive portions 108a, 108b and the garment "G" is more aggressive than the bond between conductive composition 104 and the skin of a subject "S," any removal or separation of the garment "G" from the skin of subject "S" will cause removal of electrode 100 from the skin of subject "S" prior to removal or separation of electrode 100 from the garment "G." As such, electrode 100 is removed simultaneously with garment "G."

Additionally, pressure sensitive adhesive portions 108a, 108b possess an adhesive strength permitting repeated removal of the garment "G" and the electrode 100 from the subject "S" without substantially interfering with the bond between contact layer 108 and conductive member 102. With this arrangement, the garment "G" and associated electrode 100 may be reused in subsequent procedures during a course of therapy or diagnostic applications. Moreover, electrode 100 may be used during the course of strenuous activities or non-strenuous activities without causing inadvertent disengagement of electrode 100 from the skin of the subject. Also, electrode 100 may be used during the course of high-movement activities and low-movement activities without causing inadvertent disengagement of electrode 100 from the skin of the subject.

Once electrode 100 is removed from garment "G," release liner 116 may then be reapplied to contact layer 108 to preserve hydrogel portion 108c and pressure sensitive adhesive portions 108a, 108b for subsequent uses, while release liner 114 may then be reapplied to conductive composition 104.

Alternatively, if electrode 100 is to remain in place on garment "G," following removal of garment "G," original release liners 114 or replacement release liners (not shown) may be applied to conductive composition 104 to thereby protect conductive composition 104. The release liners 114 may remain in place until the next course of treatment for the patient. In this manner, garment "G" is now provided with electrodes 100 which are properly located (or located at the same position) on the individual subject 10 for each subsequent course of treatment.

In the event that one electrode 100 is defective, said defective electrode 100 may be removed from garment "G" and replaced with a new electrode 100. In this manner, the entire garment does not have to be replaced.

Electrode 100 may be used to monitor one or more physiological characteristics of a patient or any person using electrode 100. Electrode 100 may monitor one or more of the following parameters, such as blood pressure, heart rate, or act as a weight scale, thermometer, spirometer, single or multiple lead electrocardiographs (ECG), a pulse oxymeter, a body fat monitor, a cholesterol monitor or receive a signal from an exercise machine, such as a heart rate.

In one embodiment, the present disclosure may relate to a patient monitoring system (e.g., electrode 100) which provides enhanced functional capability relative to known systems and provides a wireless communication link between a patient monitoring device, worn by a patient, and a local hub. The patient monitoring system may be adapted to monitor various patient physiological characteristics, such as blood pressure, pulse rate, blood glucose, weight, pulse oximetry and the like. The data from the patient monitoring device may be wirelessly transmitted to a local hub, which, in turn, is configured to automatically transfer the data to a remote server or computer (e.g., of a clinician), for example, over a public or private communications network.

Figure 2A:
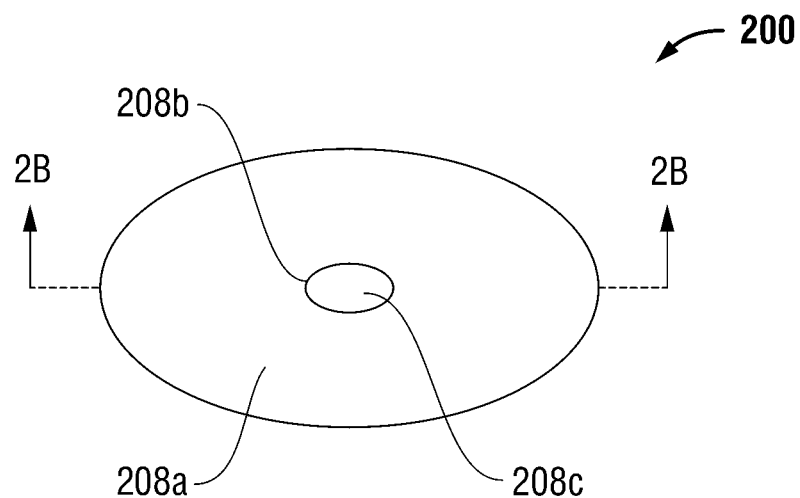
FIG. 2A is a top view of an electrode having a hydrogel portion centrally disposed on the electrode such that the pressure sensitive adhesive at least partially surrounds the hydrogel, in accordance with the present disclosure.
Figure 2B:
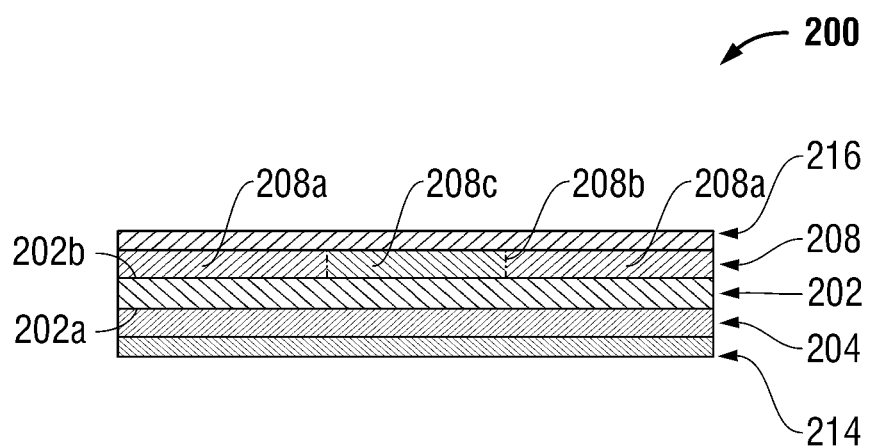
FIG. 2B is a cross-sectional view of the electrode of FIG. 2A, in accordance with the present disclosure.
Figure 2C:
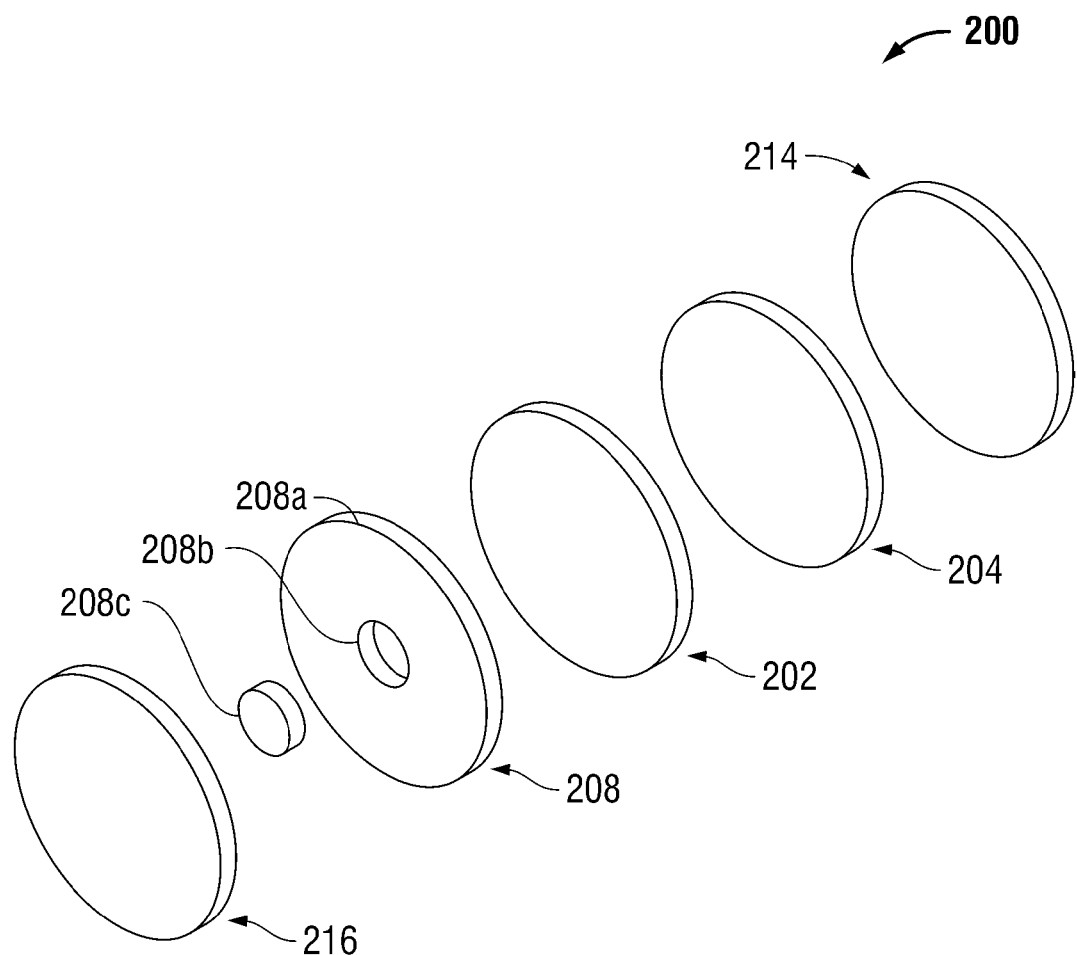
FIG. 2C is an exploded cross-section side view of the electrode of FIG. 2B, in accordance with the present disclosure.

Referring now to FIGS. 2A-2C, an electrode in accordance with another embodiment of the present disclosure is generally designated as electrode 200. Electrode 200 is substantially similar to electrode 100 and thus will only be discussed further herein to the extent necessary to describe differences in the construction and use thereof.

Electrode 200 includes a first layer or conductive member 202 defining a first or skin side 202a, relative to the subject "S," and a second or garment side 202b, opposite first side 202a; a second layer or conductive composition 204 disposed adjacent skin side 202a of conductive member 202 for application/adhesion to or contact with the skin of subject "S;" a first or skin side release liner 214 releasably secured to conductive composition 204; and a third or contact layer 208 disposed adjacent garment side 202b of conductive member 202. Once again, in certain embodiments, contact layer 208 may overlie a layer of a silver composition, e.g., Silver/Silver-Chloride.

As seen in FIGS. 2A to 2C, contact layer 208 includes a pressure sensitive adhesive (PSA) portion 208a defining a central opening 208b, and a hydrogel portion 208c disposed within, and at least partially filling, central opening 208c of pressure sensitive adhesive portion 208a. While a single hydrogel portion 208c is shown disposed substantially at the center of pressure sensitive adhesive portion 208a, it is contemplated and within the scope of the present disclosure that any number of hydrogel portions 208c may be provide across pressure sensitive adhesive portion 208a and/or that the single hydrogel portion 208c may be disposed at a location spaced from the center of pressure sensitive adhesive portion 208a.

Hydrogel portion 208c of contact layer 208 defines a conductive portion whereas pressure sensitive adhesive portion 208a defines non-conductive portion (double-coated film). Hydrogel portion 208c of contact layer 208 may be made from, for example, but not limited to, Promeon RG-63B hydrogel (available from Tyco Health Care Group d/b/a Covidien).

Pressure sensitive adhesive portion 208a is configured, adapted, dimensioned and/or selected to enable selective attachment of electrode 200 to a garment (not shown). Pressure sensitive adhesive portion 208a may be hot melt, acrylic, and/or rubber based adhesives. In one embodiment, pressure sensitive adhesive portion 208a is made substantially from non-conductive acrylic adhesives.

Similar to hydrogel portion 108c, hydrogel portion 208c has a first adhesive strength while pressure sensitive adhesive portion 208a has a second adhesive strength greater than the first adhesive strength of hydrogel portion 208c (i.e., more aggressive). In other words, pressure sensitive adhesive portion 208a is more conducive to establishing a more secure attachment of electrode 200 to a garment than hydrogel portion 208c. Thus, the adhesive characteristics or properties of pressure sensitive adhesive portion 208a relative to a garment "G" is greater than the adhesive characteristics or properties of hydrogel portion 208c relative to the garment "G."

Electrode 200 may further include a second release liner 216 is positioned to cover contact layer 208.

Figure 3:
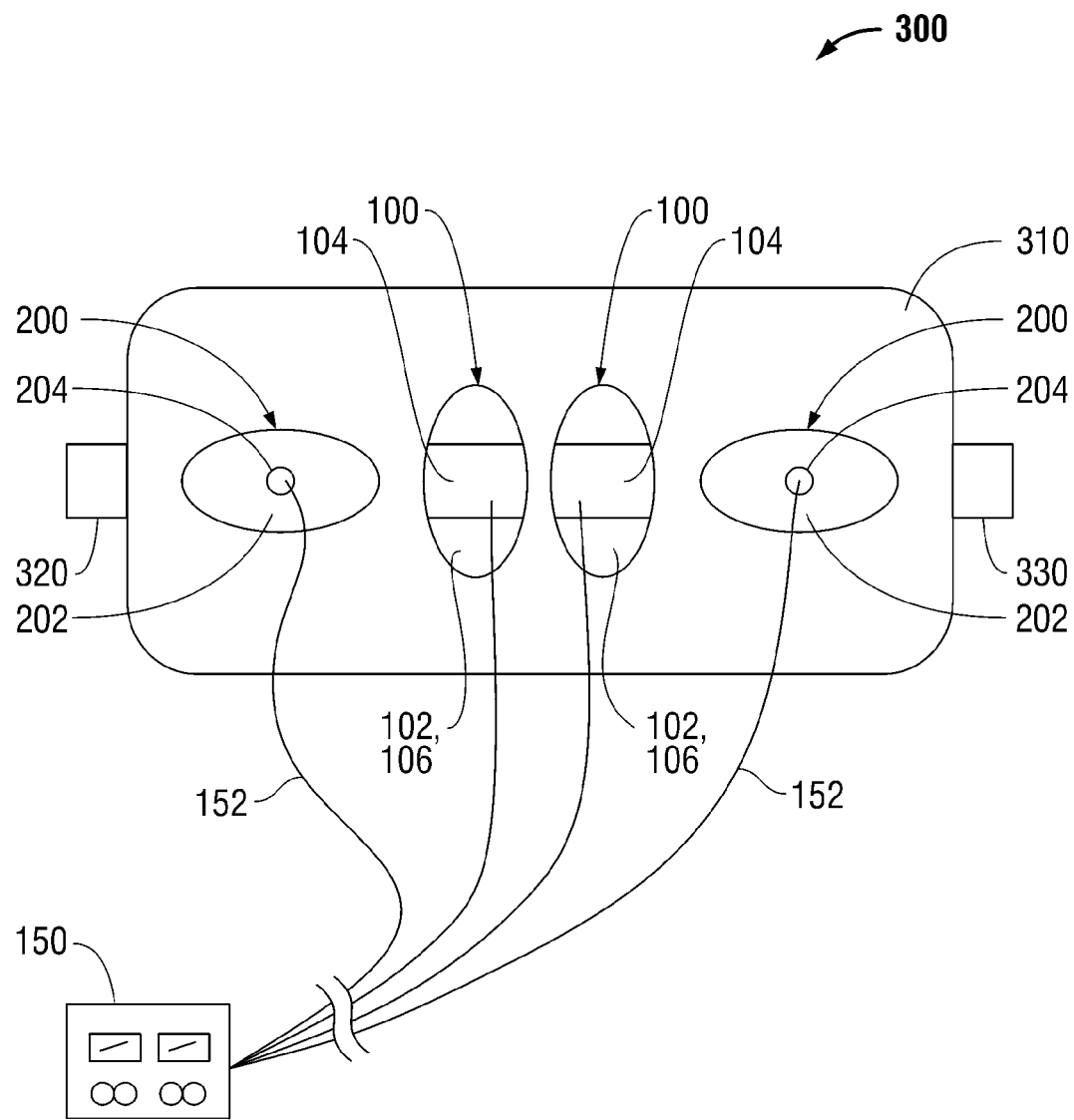
FIG. 3 is a schematic illustration of a garment for use in a medical, diagnostic, muscle stimulation, and/or therapeutic procedure, incorporating a plurality of electrodes as shown in FIGS. 1A and 2A, in accordance with the present disclosure.

Referring now to FIG. 3, a garment system for use in a medical, diagnostic, muscle stimulation, and/or therapeutic procedure, incorporating a plurality of electrodes 100, 200 as shown in FIGS. 1A-2C above, in accordance with the present disclosure is generally designated as garment system 300.

Garment system 300 includes a garment 310 (e.g., vest, belt, jacket, gown, pant, legging, etc.) having a first attachment member 320 and a second attachment member 330. First and second attachment members 320 and 330 cooperate with one another to secure garment system 300 to the subject. Garment 310, as shown in FIG. 3, includes a pair of first electrodes 100 and a pair of second electrodes 200, as described hereinabove. While a pair of first electrodes 100 and a pair of second electrodes 200 has been shown, it is contemplated and within the scope of the present disclosure that garment 310 may include any number of first electrodes 100 or second electrodes 200 or any combination thereof.

Hydrogel portions 108c, 208c of first and second electrodes 100, 200 are brought into contact with conductive elements provided on garment 310, which in turn are connected to diagnostic treatment device 150 via wires or cables 152.

As illustrated in FIG. 3, garment 310 may incorporate a plurality of electrodes 100, 200 which may be secured to an internal surface of garment 310 (e.g., within the interior of the garment 310) at predefined positions relative to the subject to provide the desired therapeutic or diagnostic effect, either prior to the donning of garment 310 or after donning of garment 310.

Garment 310 may include attachment members 320, 330 extending therefrom for selective connection and/or fixation to one another to facilitate attachment and/or wearing of garment 310 by the subject. Suitable attachment members 320, 330 may include and is not limited to hook and loop type fasteners, snaps, ties, adhesive pads, etc.

Additionally, in the event that one electrode of the plurality of first and second electrodes 100, 200 is/are defective or has/have worn out, the defective or worn out electrode may be removed from garment portion 310 and replaced with a new electrode. In this manner, the entire garment 310 does not have to be replaced and may be reused. As a result, electrodes 100, 200 may be selectively removable/interchangeable depending on the desired application and/or the determination of a defective or worn out electrode.

Figure 4A:
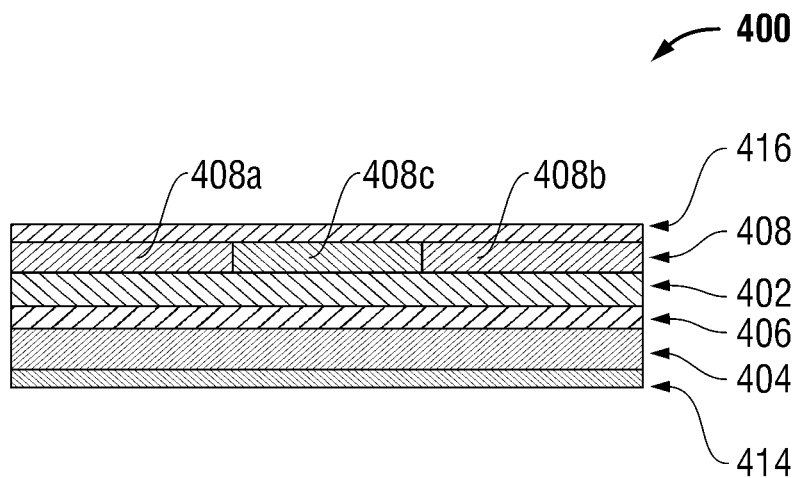
FIG. 4A is a cross-sectional view of the electrode of FIG. 1A including a silver composition layer, in accordance with an alternate embodiment of the present disclosure.
Figure 4B:
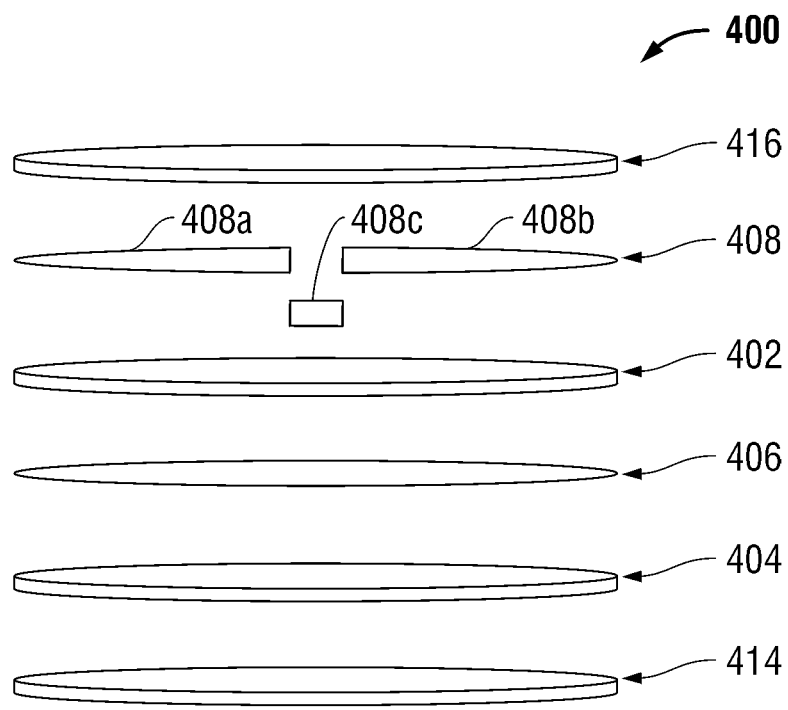
FIG. 4B is an exploded cross-section side view of the electrode of FIG. 4A including the silver composition layer, in accordance with an alternate embodiment of the present disclosure.

Referring now to FIGS. 4A and 4B, an electrode, in accordance with an alternate embodiment of the present disclosure is illustrated as electrode 400. Electrode 400 is substantially similar to electrode 100 and 200 and thus will only be discussed further herein to the extent necessary to identify differences in construction and/or use.

Electrode 400 includes a first layer or conductive member 402; a second layer or conductive composition 404 disposed adjacent a skin side of conductive member 402 for application/adhesion to or contact with the skin of subject "S;" a first or skin side release liner 414 releasably secured to conductive composition 404; and a third or contact layer 408 disposed adjacent a garment side of conductive member 402. As seen in FIGS. 4A and 4B, electrode 400 includes a layer 406 of a silver composition, e.g., Silver/Silver-Chloride (Ag/AgCl) interposed between conductive member 402 and conductive composition 404.

It is contemplated that layer 406 of silver composition may be interposed between any of the layers of electrode 400 depending on the desired application. In addition, a plurality of layers of silver composition may be disposed throughout electrode 400.

Layer 406 of silver composition may be in the form of a coating of silver/silver-chloride (Ag/AgCl) ink that is deposited or flooded on an underlying layer.

One or more reinforcement members (not shown) may be attached or positioned within or between the layers of electrode 400. The reinforcement members may be positioned either or both on the garment side or the skin of the patient side of electrode 400. In one embodiment, the reinforcement member may be used to support pressure sensitive adhesive portions 408a, 408b. The reinforcement member may be in the form of a scrim.

One skilled in the art may envision incorporating a plurality of other uniform or non-uniform conductive and/or non-conductive layers within electrode 400 (or all the other electrodes of the exemplary embodiments) depending on the desired application. For example, conductive layers may be made from a conductive carbon, aluminum, tin or any other suitable material. For instance, non-conductive layers may be plastic or insulating materials. Additionally, the entire layer need not be conductive or non-conductive. In other words, one portion of the layer may be conductive and another portion of the same layer may be non-conductive. Also, the layers may be any shape or size with respect to the other layers.

The thickness of the layers of the exemplary embodiments may be any desired thickness depending on the desired application. The thickness of the layers is preferably in the millimeter range.

It is to be understood that the illustrated embodiments are for the purpose of example, and that numerous other configurations of electrode assemblies exist. Accordingly, the illustrated and described embodiments are not intended to limit the scope of the inventive subject matter only to those embodiments.

It should also be understood that the electrode arrangements described herein can be used in connection in a wide variety of applications outside the implementations described herein. For example the electrodes described herein can be used with other known electrode arrangements. Moreover the electrode arrangements described herein can be used to detect other types of bio electric potentials on parts of the body. The electrodes described herein can also be useful for non-human applications. The electrode assembly of the present disclosure can be used to monitor at least one physiological event or characteristic of a human wearer or an animal wearer.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

Those skilled in the art, having the benefit of the teachings of the present invention as herein and above set forth, may effect modifications thereto. Such modifications are to be construed as lying within the scope of the present invention, as defined by the appended claims.

What is claimed is:

1. An electrode for selective attachment to at least one of a garment and a subject, the electrode comprising:
    a conductive member defining a first side and a second side;
    a conductive composition disposed on the first side of the conductive member, wherein the conductive composition has a first adhesive strength; and
    a contact layer disposed on the second side of the conductive member, wherein the contact layer includes a first and a second pressure sensitive adhesive portions and a conductive hydrogel portion, wherein each of the first and second pressure sensitive adhesive portions has a second adhesive strength that is greater than the first adhesive strength of the conductive composition;
    wherein the electrode is configured to be disposed between the garment and the subject in a wireless and stud-free manner such that the conductive composition is adhered to the subject and the first and second pressure sensitive adhesive portions are adhered to the garment, wherein removal of the garment from the subject results in removal of the electrode from the subject; and
    wherein the hydrogel portion separates the first pressure sensitive adhesive portion from the second pressure sensitive adhesive portion such that the first pressure sensitive adhesive portion abuts one end of the hydrogel portion and the second pressure sensitive adhesive portion abuts another end of the hydrogel portion.

2. The electrode according to claim 1, wherein the conductive composition is a hydrogel.

3. The electrode according to claim 1, wherein the hydrogel portion of the contact layer has an adhesive strength that is less than the second adhesive strength of the first and second pressure sensitive adhesive portions.

4. The electrode according to claim 1, wherein the hydrogel portion of the contact layer extends at least partially across a length of the electrode.

5. The electrode according to claim 1, wherein the hydrogel portion of the contact layer extends completely across a length of the electrode.

6. The electrode according to claim 1, further comprising a layer of a silver composition interposed between the conductive member and the conductive composition.

7. The electrode according to claim 6, wherein the layer of silver composition is a layer of Silver/Silver-Chloride (Ag/AgCl).

8. The electrode according to claim 7, wherein the layer of Silver/Silver-Chloride (Ag/AgCl) is in the form of a coating of Silver/Silver-Chloride (Ag/AgCl) ink.

9. An electrode, comprising: a first layer adapted for selective disposition on a garment; a second layer adapted for selective disposition on a subject; and a third layer adapted for disposition and electrical communication between the first layer and the second layer;
    wherein the first layer includes a hydrogel portion, a first pressure sensitive adhesive portion, and a second pressure sensitive adhesive portion;
    wherein the electrode is configured to be disposed between the garment and the subject in a wire-less and stud-free manner; and
    wherein the hydrogel portion separates the first pressure sensitive adhesive portion from the second pressure sensitive adhesive portion such that the first pressure sensitive adhesive portion abuts one end of the hydrogel portion and the second pressure sensitive adhesive portion abuts another end of the hydrogel portion.

10. The electrode according to claim 9, wherein the hydrogel portion has a first adhesive strength and each of the first and second pressure sensitive adhesive portions has a second adhesive strength.

11. The electrode according to claim 10, wherein the second adhesive strength is greater than the first adhesive strength.

12. The electrode according to claim 9, further comprising a release liner selectively and removably adhered to at least one of a surface of the first layer and a surface of the second layer.

13. The electrode according to claim 9, wherein the first layer is a first and second pressure sensitive adhesive portions each include double-coated non-conductive films.

14. The electrode according to claim 9, wherein the hydrogel portion of the first layer is a conductive hydrogel.

15. The electrode according to claim 9, wherein the second layer is a conductive hydrogel layer.

16. The electrode according to claim 15, wherein the conductive hydrogel of the second layer is similar to the hydrogel of the first layer.

17. The electrode according to claim 9, wherein the third layer is a carbon vinyl conductive layer.

18. An electrode system for selective use with a subject, the electrode system comprising:
    a garment having a first side and a second side; and
    at least one electrode for selective attachment to the first side of the garment and for selective attachment to the subject, the electrode including:
    a first layer adapted for selective engagement on the garment;
    a second layer adapted for selective engagement on the subject; and
    a third layer interposed between the first layer and the second layer, the third layer providing for electrical communication between the first layer and the second layer;
    wherein the first layer includes a hydrogel portion, a first pressure sensitive adhesive portion, and a second pressure sensitive adhesive portion;
    wherein the electrode system is configured to be disposed between the garment and the subject in a wire-less and stud-free manner; and wherein the hydrogel portion separates the first pressure sensitive adhesive portion from the second pressure sensitive adhesive portion such that the first pressure sensitive adhesive portion abuts one end of the hydrogel portion and the second pressure sensitive adhesive portion abuts another end of the hydrogel portion.

19. The electrode system according to claim 18, wherein the hydrogel portion has a first adhesive strength and each of the first and second pressure sensitive adhesive portions has a second adhesive strength.

20. The electrode system according to claim 19, wherein the second adhesive strength is greater than the first adhesive strength.

21. The electrode system according to claim 18, further comprising a release liner selectively and removably adhered to at least one of a surface of the first layer and a surface of the second layer.

22. The electrode system according to claim 18, wherein the first and second pressure sensitive adhesive portions each include double-coated non-conductive films.

23. The electrode system according to claim 18, wherein the hydrogel portion of the first layer is a conductive hydrogel.

24. The electrode system according to claim 18, wherein the second layer is a conductive hydrogel layer.

25. The electrode system according to claim 24, wherein the conductive hydrogel of the second layer is similar to the hydrogel of the first layer.

26. The electrode system according to claim 18, wherein the third layer is a carbon vinyl conductive layer.

* * * * *